(12) United States Patent
Bursavich et al.

(10) Patent No.: US 12,023,454 B2
(45) Date of Patent: Jul. 2, 2024

(54) CENTRAL VENOUS CANNULATION DEVICE AND METHOD

(71) Applicant: Board of Supervisors of Louisiana State University and Agricultural and Mechanical College, Baton Rouge, LA (US)

(72) Inventors: Jacob Bursavich, Morges (CH); Benjamin Seago, New Orleans, LA (US); Logan Daigle, Broussard, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 709 days.

(21) Appl. No.: 17/285,131

(22) PCT Filed: Oct. 14, 2019

(86) PCT No.: PCT/US2019/056075
§ 371 (c)(1),
(2) Date: Apr. 14, 2021

(87) PCT Pub. No.: WO2020/081434
PCT Pub. Date: Apr. 23, 2020

(65) Prior Publication Data
US 2021/0353910 A1 Nov. 18, 2021

Related U.S. Application Data

(60) Provisional application No. 62/746,791, filed on Oct. 17, 2018.

(51) Int. Cl.
*A61M 25/06* (2006.01)
*A61M 25/09* (2006.01)

(52) U.S. Cl.
CPC ............ *A61M 25/06* (2013.01); *A61M 25/09* (2013.01); *A61M 2205/8281* (2013.01)

(58) Field of Classification Search
CPC .................. A61M 25/06; A61M 25/09; A61M 2205/8281; A61M 25/0612;
(Continued)

(56) References Cited

U.S. PATENT DOCUMENTS

2011/0152836 A1 6/2011 Riopelle et al.
2012/0211006 A1 8/2012 Gill et al.
(Continued)

OTHER PUBLICATIONS

Cheruparambath, V., Sampath, S., Deshikar, L. N., Ismail, H. M., & Bhuvana, K. (2012).
Zhu, P., Zhang, X., Luan, H., Feng, J., Cui, J., Wu, Y., & Zhao, Z. (2015). Ultrasonographic measurement of the subclavian vein diameter for assessment of intravascular volume status in patients undergoing gastrointestinal surgery: comparison with central venous pressure. *Journal of Surgical Research*, 196(1), 102-106.
(Continued)

*Primary Examiner* — Amber R Stiles
(74) *Attorney, Agent, or Firm* — John H. Runnels (57) ABSTRACT

A device and method are disclosed for intravenous cannulation. The device employs a spring to precisely and accurately control the force and velocity imparted to a piercing needle, with mechanical constraints built into the device to precisely and accurately control the distance through which the piercing needle travels. A sheathed-needle configuration is used with an outer, echogenic needle that can be seen via ultrasound; and an inner needle used to pierce the vein. The operator releases the piercing needle with a controlled velocity, controlled force, and controlled travel distance. The device reduces the human error and complications that have previously been associated with manually piercing a vein for cannulation.

8 Claims, 6 Drawing Sheets

(58) Field of Classification Search
CPC .............. A61M 25/065; A61B 5/15003; A61B 5/15019; A61B 5/150748; A61B 5/150992; A61B 5/6852; A61B 2017/3413; A61B 2090/3925
See application file for complete search history.

(56) References Cited

U.S. PATENT DOCUMENTS

| | | | |
|---|---|---|---|
| 2013/0178711 A1* | 7/2013 | Avneri | A61M 25/0023 604/164.13 |
| 2016/0022963 A1 | 1/2016 | Belson | |
| 2017/0049991 A1 | 2/2017 | Avneri et al. | |
| 2018/0126125 A1 | 5/2018 | Hall et al. | |
| 2018/0200497 A1 | 7/2018 | Mickelsen | |

OTHER PUBLICATIONS

Kornbau, C., Lee, K. C., Hughes, G. D., & Firstenberg, M. S. (2015). Central line complications. *International journal of critical illness and injury science*, 5(3).

McGee, D. C., & Gould, M. K. (2003). Preventing complications of central venous catheterization. *New England journal of medicine*, 348(12), 1123-1133.

Eisen, L. A., Narasimhan, M., Berger, J. S., Mayo, P. H., Rosen, M. J., & Schneider, R. F. (2006). Mechanical complications of central venous catheters. *Journal of intensive care medicine*, 21(1), 40-46.

Srivatsa, K. (1992). Cannulation of vessels using a spring-loaded device. *Anesth. Analg.*, 75, 867-868.

* cited by examiner

CENTRAL VENOUS CANNULATION
DEVICE AND METHOD

This is the United States national stage of international application PCT/US2019/056075, international filing date Oct. 14, 2019, which claims the benefit of the filing date of U.S. provisional application 62/746,791, filed Oct. 17, 2018 under 35 U.S.C. § 119(e). The entire disclosure of the provisional priority application is hereby incorporated by reference.

TECHNICAL FIELD

This invention pertains to devices and methods for intravenous cannulation, particularly central venous cannulation.

BACKGROUND ART

Intravenous cannulation is a medical procedure in which a catheter is inserted into a vein, often running directly to a patient's heart for immediate drug delivery or hemodynamic monitoring. The procedure is commonly performed for emergency delivery of drugs, during extended surgeries, for anesthetic delivery, for extended drug treatments, and for patient monitoring. A common example is the extended administration of certain chemotherapy drugs.

Intravenous cannulation is a common procedure, performed up to 5 million times annually in the United States alone. However, the procedure has significant risks and is often performed incorrectly. Reports suggest that over 30% of catheters are placed incorrectly on the first attempt. Incorrect placements sometimes lead to complications, which can include puncturing the subclavian artery, puncturing the lung, and even death.

Cannulation is often assisted by ultrasonic imaging. The medical practitioner views an "echogenic" needle inside the patient's body with an ultrasound monitor. With the assistance of ultrasound imaging, the practitioner can generally guide the needle to the surface of the subclavian vein without incident. Difficulties generally arise only after the needle has reached the surface of the vein. With only a small distance within which to work, and with only a small margin for error, the user must impart a velocity to the needle sufficient to puncture the wall of the vein safely, but not so high as to continue out through the opposite wall of the vein. It is difficult for a practitioner to precisely control the force and velocity applied to the needle to successfully pierce a vein, and to traverse within the vein an acceptable distance, but not to pierce the opposite wall of the vein.

In the 1980s the Seldinger technique became standard. A typical Seldinger procedure involves: manually piercing the vein with a needle, running a guidewire through the needle into the vein, removing the needle over the guidewire, running a catheter over the outside of the guidewire into the vein, removing the guidewire, and securing the catheter in place. Using ultrasound to assist in locating the vein is fairly common, but surprisingly the use of ultrasound has not dramatically reduced cannulation complication rates. Some have suggested that the use of ultrasound itself introduces new hurdles, or that it may bestow a false feeling of confidence. Studies on complications associated with intravenous cannulations, both with and without ultrasound assistance, have reaching alarming findings. One study found a complication rate over 50% for certain types of cannulations. Another study found that subclavian cannulations (not including other cannulation locations) had a 1.5%-3.1% rate of pneumothorax (accidental piercing of the lung). This study reported a total complication rate for subclavian cannulation of 6.2%-10.7%, including the complications of arterial punctures, hematoma, hemothorax, and pneumothorax. Similar total complication rates were reported for internal jugular vein cannulations (6.3%-11.8%); and femoral vein cannulations (12.8%-19.4%).

As these procedures are often performed during surgery or in emergency medicine, complications associated with the procedures can be significant. They can lead to further complications such as cardiac arrest and even death.

The main access points for venous cannulations in humans include the internal jugular vein (accessible from the neck), the femoral vein (accessible from the upper leg), a peripheral vein (accessible from the arm), and the subclavian vein (accessible from the chest). Each location has advantages and disadvantages.

The internal jugular vein has the advantage of being relatively superficial, lying close to the skin surface, and also being relatively close to the heart. A disadvantage of using the internal jugular vein is its proximity to many muscles, organs, cartilage, and arteries, all of which can potentially be damaged during the procedure. Another disadvantage is the relative mobility of the patient's neck, which can lead to infection, to accidental removal of the catheter, and to general discomfort. Due to the associated risks, cannulation by this route requires that a physician perform the procedure.

The femoral vein has the advantage of being relatively large, and therefore allowing for larger catheters. If the femoral artery is accidentally punctured during a procedure, that complication may be addressed simply by applying pressure until bleeding is stopped. Disadvantages of using the femoral vein include its proximity to nerves and arteries, a high rate of thrombosis, difficulties in cleaning the catheter, high infection rates, high rates of accidental removal of the line, and general discomfort due to the location and mobility of the insertion point. Due to the associated risks, cannulation by this route requires that a physician perform the procedure.

The subclavian vein is the only cannulation route that has an insertion point on a relatively immobile site on the patient's body. The subclavian vein is relatively superficial, typically about 2 cm below the skin's surface; it is near the heart, which both reduces the length of guidewire required and reduces catheter misplacements. Subclavian cannulation does not require movement of the patient's head, which is helpful during emergency medicine. During hypovolemic shock the subclavian vein does not fully collapse, which give surgeons the ability to access it for longer periods of time under emergency conditions. Since the insertion location is immobile, there are fewer accidental removals, reduced infection rates, and reduced discomfort. The location is easy to clean and maintain compared to the other insertion locations. The main complications associated with subclavian cannulation arise from the proximity of the vein to the subclavian artery and to the lung; puncturing either can cause serious, even life-threatening complications. In light of the potential risks, cannulation by subclavian insertion normally requires that a physician perform the procedure.

The peripheral venous route shares some similarities with the subclavian route, but it is more susceptible to complications. The catheter is run through veins in the arm until it reaches the subclavian vein, and then through the subclavian into the heart. The peripheral vein has the advantages that it is not close to major arteries or organs, and that it is relatively superficial. Disadvantages include its relatively large distance from the heart, requiring a significant length of catheter line, which can potentially be misdirected while trying to reach the heart. Furthermore, the insertion point has an exceptionally mobile location on the patient's body, which can lead to infection, accidental removal of the catheter line, and general discomfort. This route is similar in many ways to a subclavian cannulation, but with a poor insertion point, leading to greater frequency and severity of complications.

Cheruparambath, V., Sampath, S., Deshikar, L. N., Ismail, H. M., & Bhuvana, K. (2012). A low-cost reusable phantom for ultrasound-guided subclavian vein cannulation. *Indian journal of critical care medicine*, 16(3), 163 discloses a low-cost reusable gelatin phantom that simulates subclavian vein anatomy, and its use in practicing central venous cannulation procedures.

Zhu, P., Zhang, X., Luan, H., Feng, J., Cui, J., Wu, Y, & Zhao, Z. (2015). Ultrasonographic measurement of the subclavian vein diameter for assessment of intravascular volume status in patients undergoing gastrointestinal surgery: comparison with central venous pressure. *Journal of Surgical Research*, 196(1), 102-106 disclosed that ultrasonic measurements of subclavian vein diameter correlated with central venous pressure as an indicator of intravascular volume in patients undergoing gastrointestinal surgery.

Kornbau, C., Lee, K. C., Hughes, G. D., & Firstenberg, M. S. (2015). Central line complications. *International journal of critical illness and injury science*, 5(3), 170 is a review article discussing central venous access, central lines, and associated complications and risks. See also another review article, McGee, D. C., & Gould, M. K. (2003). Preventing complications of central venous catheterization. *New England journal of medicine*, 348(12), 1123-1133.

Eisen, L. A., Narasimhan, M., Berger, J. S., Mayo, P. H., Rosen, M. J., & Schneider, R. F. (2006). Mechanical complications of central venous catheters. *Journal of intensive care medicine*, 21(1), 40-46 presented the results of a comprehensive study on the types and frequencies of complications associated with central venous catheter attempts, for example failures to correctly place the catheter, arterial puncture, pneumothorax, and hematoma.

Srivatsa, K. (1992). Cannulation of vessels using a spring-loaded device. *Anesth. Analg.*, 75, 867-868 discloses a cannulation device constructed with a central venous pressure line guide wire that acts as a spring. While the cannula is held in place on the needle, with a finger on one of the wings, the free ends of the wire are hooked over the near side of each wing. This configuration places forward pressure on the cannula. The cannula is held under tension with the wire, and the vessel is pierced as usual. Once the needle is within the lumen of the vein, signaled by a "flashback" of blood, the resisting finger can be released, and the cannula can move forward into the blood vessel. The spring and the needle are withdrawn, leaving the cannula in situ.

An unfilled need remains for improved techniques to facilitate the accurate and precise cannulation of veins, with reduced incidence of complications.

SUMMARY OF THE INVENTION

We have discovered a novel device and method for intravenous cannulation. The device provides adjustable, accurate, spring-controlled application of the precise force and velocity needed for the piercing needle; customizable mechanical constraints built into the device to precisely and accurately control the distance through which the piercing needle travels; and a sheathed-needle configuration with two needles: an outer echogenic needle that can be seen by ultrasound to help the user navigate to the vein, and an inner piercing needle used to pierce the vein. In the device's default position, the inner needle tip protrudes slightly from the end of the outer needle. When the device is primed, the inner needle is drawn within the outer needle. To prime the device, the user lifts a plunger, which pulls the inner needle into the outer needle, and in this position the inner needle locks in place through a spring-locking mechanism. The practitioner then performs a procedure such as is otherwise known in the art, for example the Seldinger procedure using ultrasound guidance, to position the outer, echogenic needle onto an outer surface of the vein. Once the outer needle is positioned on the surface of the vein, the inner needle is released by pressing a release such as a lever, which unlocks the spring-locking mechanism to allow a primary spring and the plunger to force the piercing needle into the vein. The characteristics of the spring, the mass of the spring, the mass of the plunger, and the mass of the inner needle determine the force and velocity of the piercing needle against the vein; and mechanical constraints, for example mechanical constraints built into the device's housing, control the distance through which the piercing needle can travel. The operator releases the piercing needle with a controlled velocity, a controlled force, and a controlled travel distance, all by operating a single release mechanism. The novel device removes a significant degree of human error. The swift, controlled piercing helps prevent complications associated with needle misplacement or with vein rolling, such as arterial or lung punctures.

Other steps in a cannulation procedure using the novel device may then be performed as otherwise generally known in the art for conventional cannulation procedures, for example as in the Seldinger method. Once the piercing needle is in place in the vein, a guidewire is run through a hollow pathway that traverses the device, exiting through the inner needle and into the vein; the device and needle are removed while the guidewire remains in place in the vein; a catheter is run over the guidewire into the vein; the guidewire is removed; and the catheter is then immobilized while positioned within the vein. The procedure is in most other respects generally similar to a conventional cannulation procedure, but it greatly reduces the human error commonly associated with the vein-puncturing step. With a reduced likelihood of human error, it is possible that nurses could be approved to perform central venous cannulations with the novel device.

MODES FOR PRACTICING THE INVENTION

A prototype device has been built and successfully tested in a gelatin model. The prototype device allowed the easily-adjustable, spring-controlled generation of the precise force and velocity needed for the piercing needle. Customizable mechanical constraints built into the device's housing allowed the user to precisely control the distance through which the piercing needle travelled. In one embodiment the device includes a first spring mechanism, preferably adjustable, for precisely and accurately controlling the velocity and force of the piercing needle; a second spring mechanism working in tandem with a release mechanism, such as a lever, to lock and release the first spring mechanism and hence the piercing needle; and mechanical constraints built into or affixed to the casing of the device, preferably adjustable, to control the distance through which the piercing needle moves; a sheathed needle system comprising a non-movable and relatively dull-beveled, echogenic, outer needle, within which lies a movable and relatively sharp-beveled inner needle. The echogenic outer needle enhances ultrasound imaging, and also prevents the inner needle from prematurely being exposed to or coming into contact with the skin or the surface of the vein or other internal tissues. While the subclavian vein provides the most commonly preferred route, the device can also be used to cannulate other veins, for example the internal jugular, femoral, and peripheral veins. In some embodiments the device is adjustable to allow it to accommodate various needle gauges, needle lengths, needle piercing forces, needle velocities, and needle travel distances. The device may be used in human or veterinary medicine, and in both adult and pediatric medicine. The device could prevent hundreds of thousands of complications annually, some of them potentially life-threatening.

Working prototypes have been designed with CAD and have been 3D-printed in PLA. A prototype has been successfully tested on a literature-based, gelatin model such as is used for training medical students. The gelatin model incorporated plastic tubing to mimic veins, arteries, and internal organs. The needle of the prototype device successfully and repeatably punctured the simulated vein with a precise and accurate needle travel distance and force. The device will next be tested on cadaveric models (animal and human); then it will be tested on animals in vivo; and then it will be tested on humans in vivo; all in accordance with governing laws and regulations.

Outer Needle

The outer needle, which is preferably echogenic, allows the practitioner to locate the needle via ultrasound imaging. Echogenic needles are commercially available. They typically have surface micro-etchings, or a polymeric coating with microscopic bubbles, both of which enhance ultrasound reflectivity. The outer needle has a relatively dull bevel; "relatively dull" means simply that because there is an inner bore large enough to accommodate the inner needle, the outer needle has a smaller cutting edge for piercing skin, blood vessels, or other tissues than it would have with a narrower bore. The outer needle is sufficiently sharp to pierce the skin, but is unlikely to damage internal structures or to accidentally pierce the vein prematurely. The outer needle preferably remains stationary during use, i.e., it retains a fixed position relative to the larger device.

Inner Needle

The inner needle, the piercing needle, can be an otherwise standard hypodermic needle, such as are commercially available for cannulation procedures. The inner needle is small enough to fit within the inner bore of the outer, echogenic needle, but is large enough to allow a guidewire in turn to pass through its inner bore. The inner needle is sharp enough to easily pierce the target vein. When the primed device is triggered, the inner needle is forced from the outer, echogenic needle into the vein with an accurate and precise force, velocity, and travel distance. Sheathing the inner needle within the echogenic needle before triggering helps ensure that the inner needle only contacts the vein at the proper time, limiting the potential for injury to other tissues.

Customization by Modifying the Casing

In one embodiment, the device can be adapted for "universal" usage, that is, to be compatible with some or all of the different types and sizes of needles that would typically be used for various cannulation procedures. Standard gauge needles include a standard needle hub. (The hub is the component that would, for example, typically attach a standard needle to a standard syringe.) The prototype device comprised a plunger that is in some ways analogous to the plunger of a conventional syringe. The plunger and housing can be adapted to fit either standard needle hubs, or other sizes of hub, gauge, shaft length, or bevel types. The casing of the prototype device also controlled the distance through which the inner needle travelled past the end of the outer needle. Mechanical constraints within the housing of the device determined the distance through which the primary compression spring could move. Other mechanical constraints controlled the distance through which the piercing needle could move. Thus the device controlled both the distance through which the inner needle can travel, and the force that the needle exerts on the vein. The constraints also inhibit unwanted oscillation of the plunger spring and hence inhibit oscillation of the inner needle that might otherwise occur if the plunger spring were allowed to fully extend.

Using multiple, nonidentical casing molds, or customizable casing molds allows practitioners the flexibility to choose specific needles, catheters, and other components they may prefer or with which they are already familiar. These options also allow varying the inner needle's force, velocity, and distance traveled. For example, pediatric veins are smaller than adult veins. In veterinary applications, a wider range of sizes may be needed; larger mammals typically have larger and thicker veins, requiring greater force and travel distance; while the opposite is true for smaller mammals. In practice, a practitioner could request a device based on the gauge of the needle needed and the type of patient (as examples: pediatric, adult, or large dog). Using this information, the dimensions of the device and the positioning of the mechanical constraints in the housing could be configured to meet specific needs.

Components of a Prototype Embodiment

Figure 1:
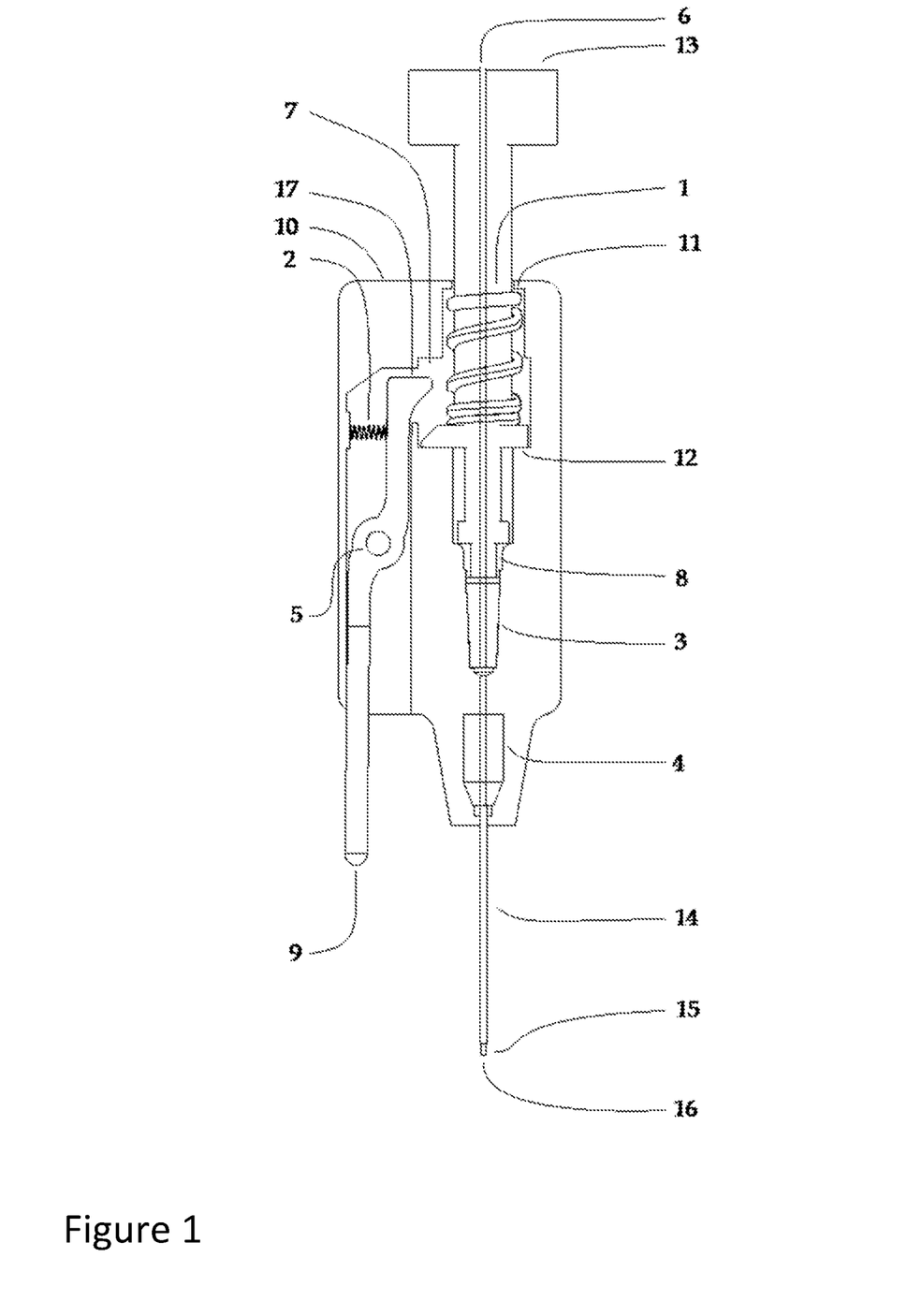
FIG. 1 depicts a cutaway view of an embodiment of a device in accordance with the present invention.
Figure 4:
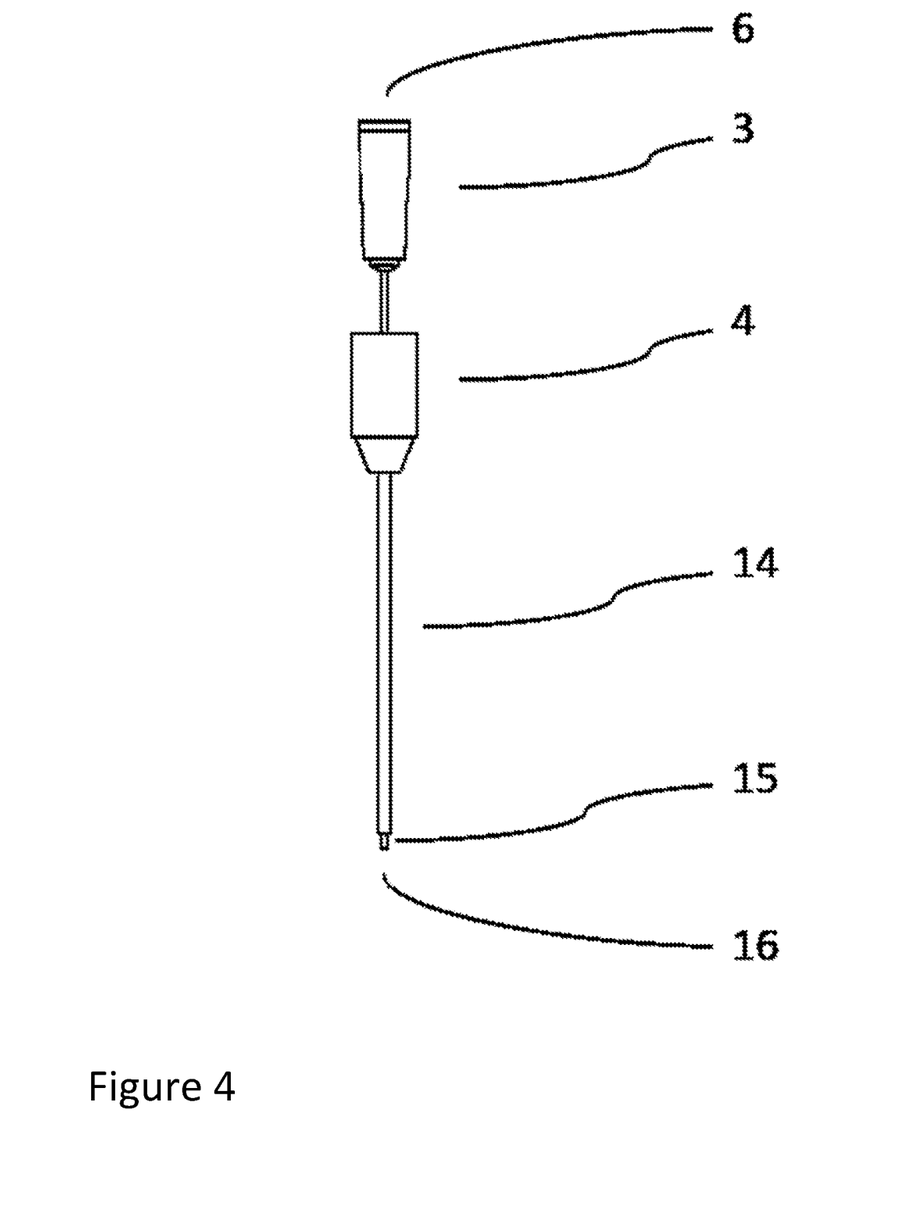
FIG. 4 depicts an enlarged view of an embodiment of the piercing needle and outer needle.

A cross-sectional view of one embodiment of a device in accordance with the invention is depicted in FIG. 1. The embodiment comprised a plunger 13, a plunger top 6 with an insertion point for a guidewire (not shown) that passes through the device and out of the end 16 of the device, and a bottom 8 in which the hub of the inner piercing needle 15 is placed, a release lever 5 with an end 17 that holds plunger 13 in place, and another end 9 that the user pushes to release plunger 13, the casing 10 for the device, mechanical constraints 11 and 12 built into the casing 10 to constrain the displacement of plunger 13 and the location 7 where plunger 13 rests atop release lever 5, a primary compression spring 1, a secondary compression spring 2, an outer echogenic needle 14 with its hub 4, an inner piercing needle 15 with its hub 3. FIG. 4 shows an enlarged view of piercing needle 15 and outer needle 14, and how the former passes through the latter.

A vented screw (not shown) within plunger top 6 connects plunger top 6 to the bottom of plunger 13, allowing for easy assembly and maintaining a passage for a guide wire to pass through the plunger top 6 and exit through the end 16 of the device. Generic screws and nuts were used to hold the housing casings together. Other fasteners known in the art may be used in lieu of screws and nuts.

Plunger 13 has multiple functions. The primary compression spring 1 that imparts velocity and force to piercing needle 15 is positioned along the shaft of plunger 13 in such a manner that compression spring 1 is restrained from extending to its full free length. Plunger 13 includes a cylindrical hollow interior along its vertical axis through which a guidewire (not shown) may travel. A ledge on the side of plunger 13 is adapted to extend past release lever 5, while being restrained from moving past release lever 5 before release lever 5 has been manually released by the user, thus allowing primary compression spring 1 to lock in a compressed state. The end of plunger 13 is adapted to engage the hub of piercing needle 15; if desired the end of plunger 13 can be adjusted to accommodate virtually any type of needle hub 3. The diameter and length of the shaft of plunger 13 can be modified to accommodate different springs 1, to increase or decrease the spring load, and to increase or decrease the velocity and force that piercing needle 15 applies to the vein when primary spring 1 is released from the compressed position.

Plunger top 6 is optionally separable from plunger 13, to facilitate positioning primary compression spring 1 around the main shaft of plunger 13. Plunger top 6 can also act as a finger-hold that the operator can pull to prime and lock primary compression spring 1 into a compressed state (or more compressed state). The plunger top 6 also has cylindrical hollow interior along its vertical axis. A vented screw (not shown) is set inside the hollow cylinder, positioned within the plunger to connect both components of plunger 13 after primary compression spring 1 has been positioned on the shaft of plunger 13. The guidewire (not shown) is fed by the user manually through the hollow interior in plunger 13 at position 6, continuing through plunger 13 and piercing needle 15, and exiting through an opening at the end 16 of piercing needle 15 and into the lumen of the vein after the vein has been punctured.

Alternative embodiments could, for example, include a guidewire coiled and contained in or on the device itself, so that the operator could twist a dial with the same hand used to hold the device to cause the guidewire to uncoil directly through the device, further simplifying the device's use. In the prototype device depicted in FIG. 1 the guidewire had not been thus integrated.

Release lever 5 is positioned on and is rotatable around the axis of a cylindrical hub positioned in or on the casing. Release lever 5 is held in place by secondary compression spring 2, which by default holds release lever 5 in the locked position. When the user pulls plunger 13 up, release lever 5 is displaced, secondary compression spring 2 is compressed, and release lever 5 rotates around its cylindrical pivot. After the user pulls plunger 13 out to its maximum extension (determined by the constraints of the casing 11), release lever 5 then returns to its default position and is held there by secondary compression spring 2. Plunger 13 then rests at position 7. In this state, piercing needle 15 is sheathed inside echogenic needle 14. When the user moves the release lever 5 to position 9, plunger 13 is no longer held in the locked position, and primary compression spring 1 is free to extend. Piercing needle 15 then extends outside echogenic needle 14 with a controlled distance and velocity. The portion of release lever 5 that comes into direct contact with the ledge on plunger 13 incorporates a filet to promote a smooth transition between locked and released positions. In the prototype device, release lever 5 is thicker in the vicinity near the cylindrical hub. This thickening strengthens the lever to reduce the likelihood that excessive force on release lever 5 might cause it to mechanical failure, for example from excessive force applied by the user on release lever 5, or from plunger 13 applying force at position 17.

Figure 2A:
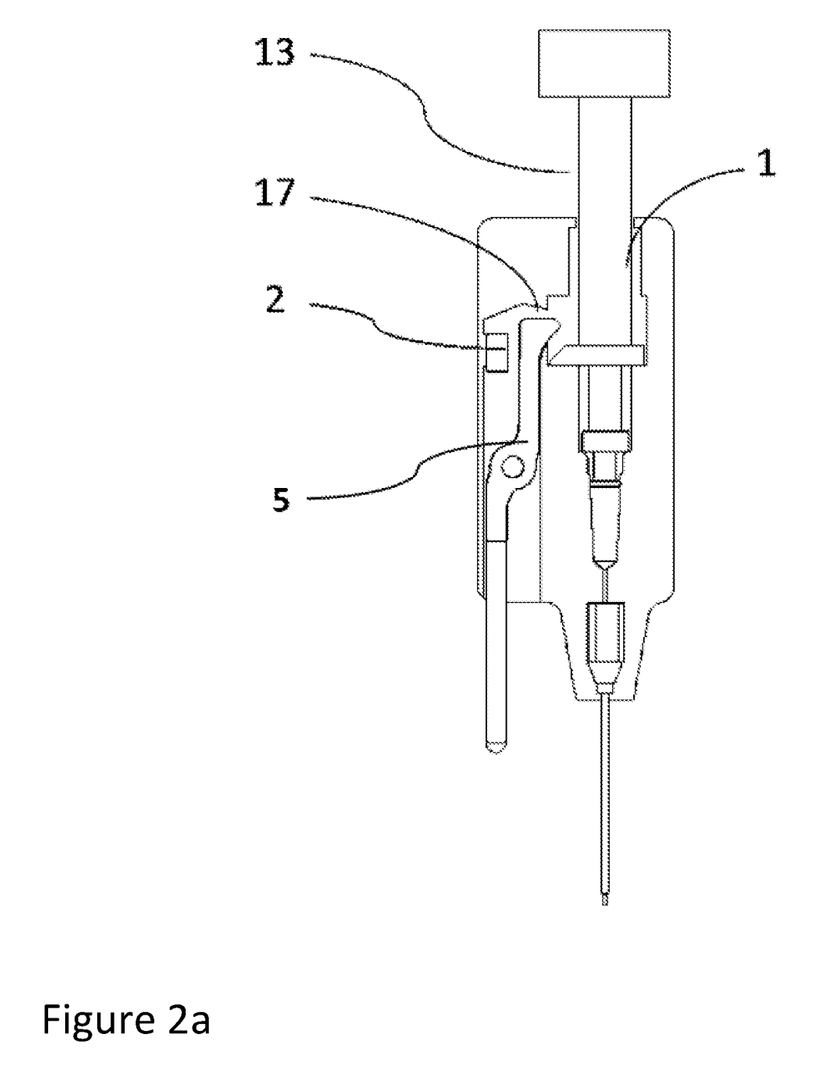
FIG. 2A depicts a prototype embodiment in the default or resting position.
Figure 2B:
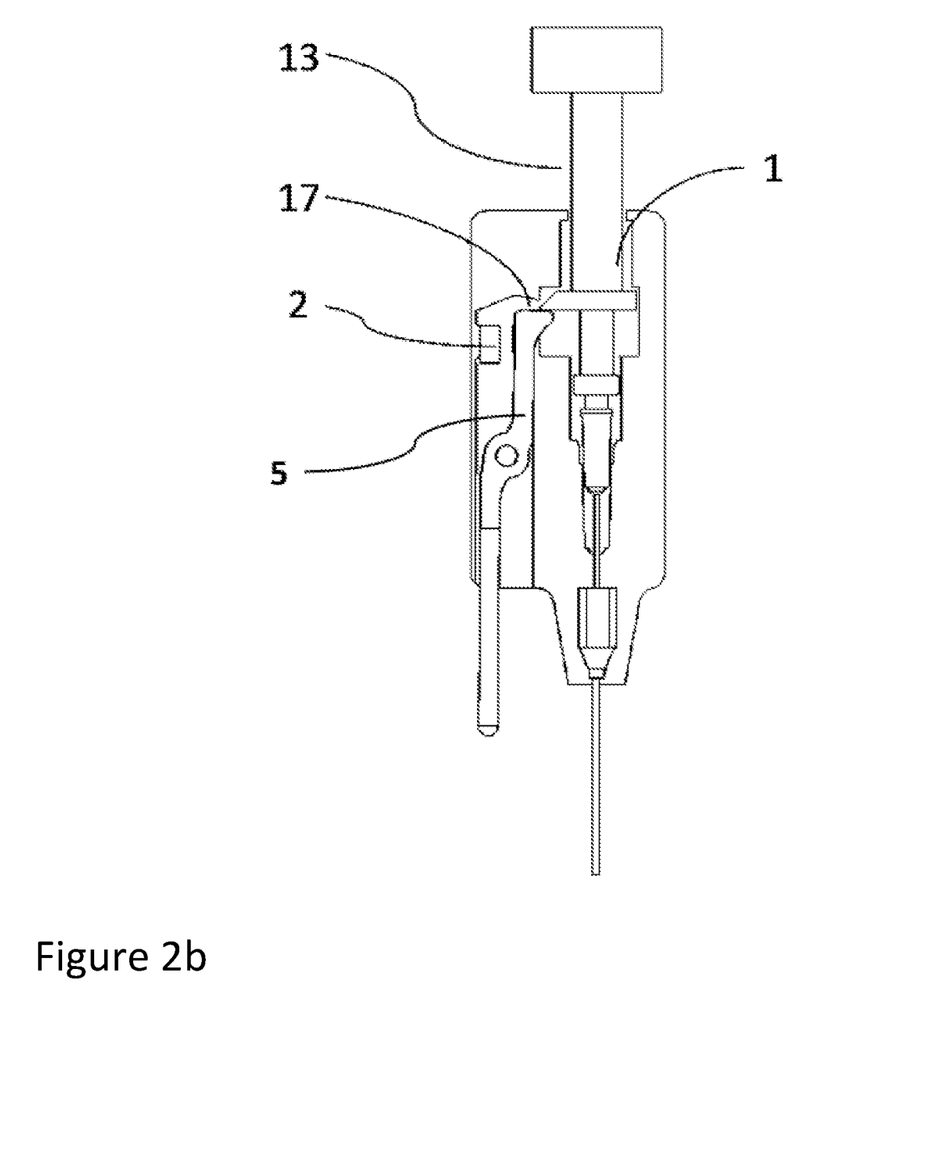
FIG. 2B depicts a prototype embodiment in the primed position, ready to be deployed.
Figure 2C:
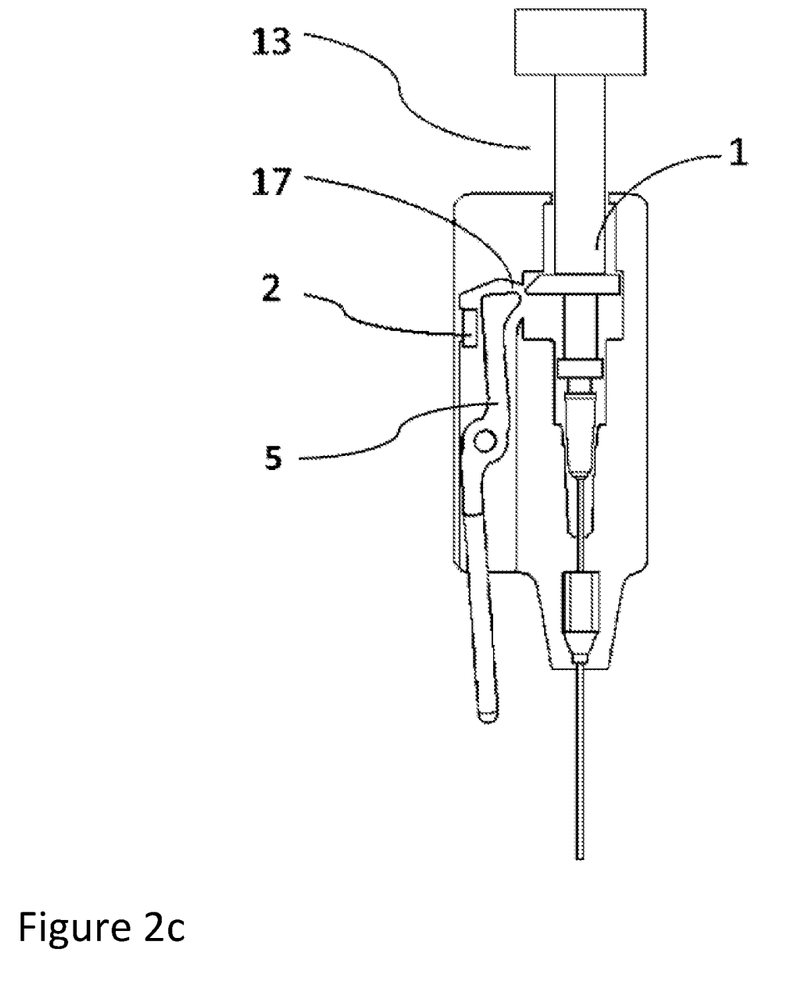
FIG. 2C depicts a prototype embodiment immediately after it has been triggered.

FIG. 2A depicts the prototype embodiment in its default or resting position. FIG. 2B depicts the prototype embodiment in the primed position, ready to be deployed. FIG. 2C depicts the prototype embodiment immediately after it has been triggered. In each of FIGS. 2A through 2C note particularly the positions of plunger 13 and release lever 5.

A prototype embodiment has been fabricated in polylactic acid (PLA) using a 3D printer. Alternatively, the device could be manufactured from a stronger material, such as sheet metal or a more durable polymer, through means known in the art such as polymer injection molding or sheet metal stamping. In alternative embodiments, pushable buttons or rotatable dials are incorporated into the device for releasing the compression spring lock, in lieu of the lever that was used in the prototype device. Future prototypes may employ a button rather than a rotatable lever to make the device more ergonomic and to make the release mechanism more easily accessible.

The device's housing casings are preferably multifunctional. They hold the internal components in place, and they also supply mechanical constraints that help control the device's operation. The constraints hold the primary compression spring in place in its relaxed state, they hold the primary spring in its compressed state, they prevent the primary and secondary springs from overextending, they control the distance through which the piercing needle travels, they limit the angle through which the release lever can move (protecting the lever against breakage from overextension), they stabilize the echogenic needle and hold it securely in place, they confine the primary compression spring in a compressed state to inhibit oscillation, and they provide a secondary redundant constraint to restrict the piercing needle from overextending. The casing in the prototype device comprised two components that were mirror images of one another, except that the cylindrical hub positioning the release lever was present on only one of the two components. The housing components can optionally be modified so their dimensions allow for a range of springs and needles, and customizable variations in the force applied by the piercing needle to the vein, in the velocity imparted to the piercing needle, in the echogenic and piercing needles' gauges, in the echogenic and piercing needles' shaft lengths, and in the echogenic and piercing needles' overall design, including variations in hub type and bevel shape, and in the distance through which the piercing needle travels.

Figure 3:
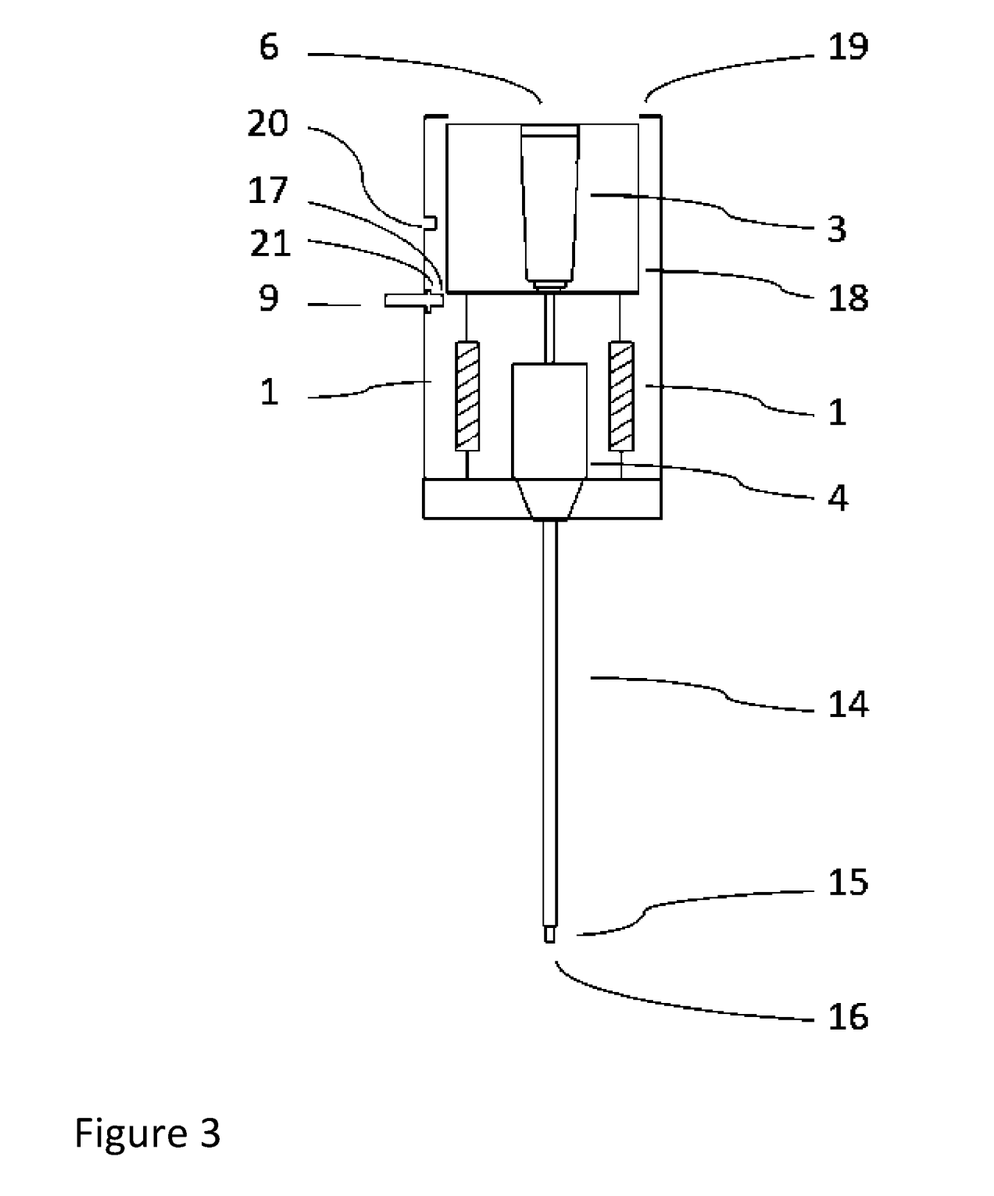
FIG. 3 depicts an alternative embodiment employing a torsion spring rather than a compression spring.

In an alternative embodiment, depicted in FIG. 3, a torsion spring rather than a compression spring is incorporated to reduce the overall size of the device. Where corresponding reference numerals are the same, the components depicted in the embodiment of FIG. 3 correspond to the like-numbered components for the embodiment depicted in FIG. 1. The overall configuration shares many similarities, but instead of a compression spring to force piercing needle 15 from the bore of echogenic needle 14, single or multiple torsion spring(s) 1 are attached to the bottom of plunger 18 and to the bottom of casing 19. A spring locking mechanism can be incorporated, similar to that previously described, allowing the user to manually displace plunger 18, and thus the torsion spring(s) 1, to lock and hold the extended torsion spring(s) 1 until the user manually releases the locking mechanism. Plunger 18 holds the hub 3 of the piercing needle 15 in place. Torsion spring(s) 1 are in a state of constant extension, never being allowed to fully compress, and thereby inhibiting any oscillation of piercing needle 15. The locking and releasing steps are performed by the user in a manner generally similar to that for the embodiment of FIG. 1, described previously. The user moves release lever 9 into a locked position at indentation 20. The end 17 of release lever 9 holds plunger 18 and thence piercing needle hub 3 in place until released. The plunger 18 is constrained by the casing 19 to move in a single direction, and only through a limited degree of displacement. Release lever 9 has extensions 21 to inhibit it from moving outside the device. The release mechanism can be modified to allow alternative ways to lock and release plunger 18. The user moves release lever 9 and twists it into position at indentation 20, thus locking it until it is released. In this state piercing needle 15 is sheathed inside echogenic needle 14, and torsion spring(s) 1 assume their extended state. The user then performs the procedure as generally described previously. The user positions echogenic needle 14 on the outside of the vein, and then releases lever 9, returning torsion spring(s) 1 to the less extended state, releasing plunger 18 to return to its default position, and allowing piercing needle 15 to leave echogenic needle 14 at a controlled distance and velocity. The user then inserts a guidewire through the top 6 of the device into the hub 3 of piercing needle 15, traveling through hub 4 and shaft 14 of echogenic needle 14 and exiting the piercing needle at end 16. This embodiment of the device allows for a significantly reduced size as compared to the embodiment of FIG. 1—a size whose total length is comparable to the length of piercing needle 15 itself. Reducing the size of the device not only makes the device easier to use; it can also help the procedure feel more "familiar" for a user who is accustomed to performing intravenous cannulations using just a conventional needle. This smaller embodiment also makes it possible for the user to more easily see the expulsion of venous blood, or "flashback" of blood, from the top 6 of piercing needle 15, which is a commonly-used indication of a successful venous penetration.

In a further alternative embodiment, the piercing needle is positioned by the practitioner on a modified plunger instead of being included as a component of the device. The plunger is modified so that the piercing needle is constrained relative to the position of the plunger after the practitioner has manually attached it to the device. The needle may be removed after usage. This modification promotes reusability of the device, and allows the practitioner more easily to select from a range of needle gauges.

Housing Casing Constraints and Release Mechanism

It is important to control the distance the piercing needle travels, the velocity of the piercing needle, and the applied force of the piercing needle upon the vein. Too short a travel distance can cause issues when attempting to place the guidewire and catheter inside the vein, and too great a travel distance can result in puncturing the opposite wall of the vein, or puncturing other internal tissues or organs such as an artery or a lung. Too high a velocity or applied force can cause damage and structural instability, or make the device difficult for the operator to manage, while too low a velocity or applied force may prevent the inner needle from successfully piercing the vein, or cause the vein to "roll." The novel device can precisely control all these factors. The travel distance is controlled by mechanical constraints in the casing, and the shaft lengths of the piercing and echogenic needles. The velocity and applied force are controlled by a spring with known mechanical properties, together with constraints on the distance through which the spring is allowed to compress and extend, and the masses of the relevant components. The prototype device has been tested with various springs. It was designed to accommodate a variety of springs to allow variations in the imparted force and velocity. Oscillations in the primary compression spring are inhibited by mechanical constraints that prevent the spring from extending to its natural free length. Constraints are also placed in the housing casing to prevent the spring from compressing or extending too far, which could cause undesired changes to the spring's properties, thus enhancing the ability to reuse the device.

Stability and Precision of Fabrication

The fabrication material should be selected to make precise and accurate: the distance travelled, the velocity imparted, and the force imparted. Thermal expansion and water absorption properties should also be considered, as these properties can affect dimensional stability. Even a single-use, disposable embodiment will typically undergo at least one cycle of autoclave sterilization, a procedure that exposes the device to both heat and moisture. Furthermore, the material is preferably cost-efficient and well-suited for use with modern fabrication techniques. Taking such factors into consideration, medical grade polyether ether ketone (PEEK) is a preferred polymer for multiple-use applications; and polyvinyl chloride (PVC) is a preferred polymer for single-use applications. As the housing casing itself is not intended to directly contact the patient, and it is not intended to directly deliver any liquids or medications during normal use, concerns over potential release or leakage of monomers, plasticizers, or similar compounds from the casing should be minimal and inconsequential.

For prototyping, however, a device was 3D-printed with polylactic acid (PLA), a common, biodegradable, thermoplastic, aliphatic polyester. PLA is commonly used in biodegradable medical devices and implants. It is easy to use as a fabrication material.

With a vented access hole in the top of the plunger, and an access hole through the central axis of the device, the guidewire can be fed directly into the piercing needle and thence into the vein, with no need to move the device, the needles, or other components once the piercing needle has been introduced into the vein.

Catheter lines are often left in a patient's body for hours or days. The device itself should therefore preferably be removable after the guidewire has been inserted. Then it may either be disposed of, as would a regular syringe or other a single-use device; or it may be autoclaved for reuse as a multiple-use device.

Size and Shape

It is preferred that the size and shape of the device should be ergonomic, and that the device should be equally usable by left-handed or right-handed operators.

We varied several aspects of the prototype device to investigate variations that worked well, those that did not work so well, and those that were preferred. We varied the shape of the device, the type of locking mechanism, the type of oscillation inhibitor used, the mechanism used to open the casing, the attachment mechanisms for various components, the mechanism to adjust the needle plunge depth, whether the device was single-use or multiple use, and the route for removing the needle.

One possible shape for the device is "thin-cylindrical," generally similar in overall size and shape to a thick writing pen. This shape allows the device to be held and operated with one hand; and allows the user to keep a strong grip on the device during operation. An alternative choice would be a "pipette shape" that could provide even better grip via a variable cross-section, but that could suffer a tradeoff in reduced dexterity and increased bulkiness. Other alternative shapes are also possible.

The preferred locking mechanism is spring-based and works in tandem with a lever or button to lock and release the plunger, a mechanism that is simple, efficient, and may be conveniently located for the user's thumb.

A preferred avenue to inhibit oscillation of the spring and the piercing needle is to mechanically limit the free length expansion of the spring.

Hinges are preferred to open and close the case, in part because they can be built without separate internal components, simplifying the design.

It is preferred for the top component of the device casing to be removable to allow for adding or removing needles, and thus to be a multiple-use device.

In a preferred embodiment, the needle plunge depth is static (not adjustable by the operator), because a single, fixed plunge depth will work well for most adult human patients: The inner needle may be set to protrude approximately 1.25 mm from the tip of the outer needle, a distance that should work well for nearly all adult humans during subclavian cannulation, for example. Alternatively, the needle travel depth can be made adjustable by the operator, for example by introducing a twistable screw on the plunger, and allowing a knob accessible from outside the casing (along with a unit indicator) to control the twist (and thus the lengthening or shortening) of the screw.

Our initial prototype device was designed for single-use operation, both for ease of fabrication and to avoid potential issues with contamination and infection that could arise with multiple-use devices. Whether a single-use or multiple-use device is preferred depends both on economic considerations and on the particular setting where a device will be used.

The initial prototype device allowed simple mechanical removal of the needle by disassembly of the device housing. Alternatively, other embodiments might include a mechanism to remove the needle(s) in a fashion similar to that used for many laboratory pipettes to eject a tip, or other mechanisms known in the art for removing a needle.

As the prototype was designed and constructed, some of our initial design choices/preferences were modified. The finished prototype was a hybrid between a thin cylindrical shape and a pipette shape. It did not allow the end-user to readily open the casing. It was designed as a single component. It lacked any attachment method for multiple components. It was not necessary to remove the needle; instead, the device was configured to allow the guidewire to run through the length of the entire device, including the needle, allowing a Seldinger-type procedure to be performed without unnecessary additional steps, and allowing the device to be operated as a single-use device and to be disposed of after use.

Design Considerations

"Universality" was a consideration in designing the prototype. The prototype was designed to be compatible with existing medical equipment, such as ultrasound transducers and commonly-used needles, guidewires, and catheter lines. The device is readily customized for a range of common and specialized needles, guidewires, and catheter lines. The first prototype employed a 22-gauge piercing needle and an 18-gauge echogenic needle; it accommodated guidewires up to 0.39 mm diameter; and it would be compatible with all commonly-used sizes of catheter lines. Although its use is not so limited, the prototype device was designed specifically to be compatible with procedures and equipment used in subclavian cannulation procedures for human adults.

The overall size of the device was another consideration in designing the prototype. Ergonomic designs are important to encourage acceptance by medical professionals. The final prototype design was easy for a single operator to use. The device should reduce costs by reducing procedure times and complication rates. Due to the significant reduction in human error and resulting reduction in the number of catheter misplacements and the required venous piercing attempts, the invention will reduce the overall time required for intravenous cannulations.

Sterilization is also a consideration. Autoclaving—treatment with high pressure, heat, and saturated steam—is commonly used to sterilize medical equipment. Only certain materials may be safely autoclaved. The materials used in the prototype were all chosen to be compatible with autoclaving without significant dimensional instability.

Measurable Objectives

Measurable objectives for the prototype included a repeatable velocity, a repeatable force, and a repeatable travel distance for the piercing needle; as well as ease of use.

More specifically, the chosen tolerances for prototype testing were: The velocity should be repeatable within a tolerance of ±5% at least 95% of the time. The travel distance for the piercing needle should be 3.5 mm within a tolerance of ±5% (i.e., a range between 3.325 to 3.675 mm) at least 99% of the time. Repeatability of the plunge depth is important for patient safety. Too great a travel distance could cause double-wall piercing of the vein and other internal injuries, while too short a travel distance could result in a failed puncture of the vein, which could necessitate additional piercing attempts and thereby increase the time required and the likelihood of complications. The length that the piercing needle travels outside the echogenic needle may optionally be made adjustable, but even if adjustable it should be made precise and repeatable. To ensure practicality of the device, the time to prepare the device for use should be under two minutes. The ability to be set up quickly is not only a measure of the design quality, but can be very important in medical procedures. Even short delays can sometimes have devastating consequences, especially in emergency medicine when cannulation is used to deliver life-saving drugs in the fastest way possible, or to provide real-time monitoring of patient stability.

Initial Calculations

Initial calculations began with the average distance the piercing needle should travel to puncture the subclavian vein consistently. Literature reports that the diameter of the subclavian vein for both adult men and women generally ranges from 4.8 to 9.2 mm, with healthier patients tending to have larger-diameter veins. The device was configured to allow a total travel distance of 3.5 mm±5%, i.e., 3.325 to 3.675 mm. This distance was selected for the prototype to ensure a single-wall puncture of the subclavian vein, largely independent of the angle of approach when the outer needle is positioned directly above the center of the vein. If the piercing needle does not penetrate the vein at a direction normal to the vein's surface, but instead approaches the vein at a shallower angle, there is a shorter distance the needle will travel within the lumen before it pierces the wall of the vein a second time. By reducing the distance through which the piercing needle travels, this risk is reduced. Likewise, if the piercing needle is off-center when it punctures the vein, there is also a shorter distance through which the needle can travel before reaching piercing the wall of the vein a second time, and again it is preferable to keep the travel distance short. Based on these considerations, we chose 3.5 mm as a preferred travel distance for the piercing needle for subclavian cannulations of adult humans.

The outer needle's inner diameter should be large enough to accommodate the inner needle, and the inner needle's inner diameter should be large enough to accommodate the guidewire. Literature review showed that 16 to 22-gauge needles are typically used for cannulation procedures. (Smaller gauge numbers correspond to larger needle diameters.) A 16-gauge needle has a 1.65 mm outer diameter and a 1.19 mm inner diameter. A 22-gauge needle has a 0.72 mm outer diameter and a 0.39 mm inner diameter. We selected an 18-gauge outer needle (inner diameter 0.84 mm) to accommodate a 22-gauge inner needle (outer diameter 0.71 mm). Guidewires typically have diameters much smaller than 0.39 mm (the 22-gauge inner diameter). 18-gauge and 22-gauge needles were chosen for the initial prototype, because they had suitable inner and outer diameters, and also because they were commercially available with shaft lengths consistent with the other design parameters of our prototype device. The device may be customized or modified for other needle gauge sizes, needle shaft lengths, piercing needle travel distances, generated forces, and velocities. (The particular dimensions given in this paragraph are based on standardized values. Reported dimensional tolerances in the manufacturing processes have also been accounted for, and should not present any problems arising from the relative difference in the sizes of the inner diameter of the one needle and the outer diameter of the other, because the reported tolerance values are small.)

Two types of polymer were chosen for prototype embodiments, one intended for a multiple-use, more expensive version; and the other for a single-use, less expensive version. The multiple-use version was made from polyether ether ketone (PEEK) (Tecapeek MT). This polymer was chosen for its durable material properties. PEEK has a linear thermal expansion rate of $2.0*10^{-5}$ ($K^{-1}$), and moisture absorption of about 0.04% (these two values are both close to those for steel). The manufacturer reports that Tecapeek MT polymer can withstand approximately 1,500 autoclaving cycles without failure and without significant changes in mechanical properties. PVC was chosen for the less expensive, single-use prototype. PVC is commonly used for medical devices. It has a linear thermal expansion rate of $5.76*10^{-5}$ ($K^{-1}$), and a moisture absorption rate of 0.06%, indicating that PVC is also a reliable and durable polymer. The single-use design is autoclaved once, packaged, then opened only when it is time to perform a cannulation. The single-use device is fully-assembled, with needles included, and is ready to use immediately upon opening the packaging. For prototyping purposes, the polymer used was PLA, and the device was 3D-printed. However, both Tecapeek MT and PVC can readily be used with common fabrication equipment and techniques, such as injection molding and other polymer manufacturing techniques known in the art.

Prototype Testing

The prototype device was tested in a realistic working environment. Future tests will use ultrasound-guided, subclavian cannulation on fresh cadaveric specimens; followed by in vivo testing of animals, followed by in vivo testing in humans; all in accordance with applicable laws and regulations.

Prototype testing used a model from literature, a model that is commonly used by medical students. The model is gelatin-based, with encased plastic tubing and balloons to represent veins, arteries, and lungs. The tubing and balloons were filled with colored dye to provide visual indication of puncture sites.

Multiple tests were conducted on the gelatin-based model. The tubing thickness of the simulated veins was slightly larger than average vein thickness. The device was nevertheless able to carry out single-wall punctures on the simulated veins consistently and without difficulty.

Microscopic imaging with ImageJ software captured and analyzed the velocity and travel distance of the piercing needle. The device was primed, triggered, and released for 15 separate events. Each event was imaged and measured 15 individual times, for a total of 225 measurements. The mean travel distance was 3.49 mm, with a minimum of 3.45 mm and a maximum of 3.52 mm, well within the target range of 3.50 mm±5% tolerance. Unfortunately, the microscopy camera did not have a sufficiently high frame rate to make meaningful velocity measurements in the initial tests.

Based on initial results with the gelatin-based model, a spring force of about 21.7 N is preferred for a single-wall puncture in adult humans. Within limits, too little force would be expected to cause more problems than too much force. The prototype device allows one to apply greater force if desired, without over-extending the travel distance of the piercing needle. We have not (to date) tested higher spring forces, because (within limits) we do not believe higher forces should present issues.

Materials Used in the Prototype Embodiment

The compression spring used to impart force to the piercing needle was a Springsfast item number C18-047-032, with an OD of 13.7 mm, an ID of 11.3 mm, and a nominal spring load of 26.7 N. Additional springs were purchased from Springfast—item number C18-055-02 and number C18-059-032, with nominal spring loads of 53.4 N and 66.7 N, respectively—but the two stronger springs have not been used to date, because piercing was already consistently successful with the weakest of the three compression springs. The compression spring used to operate the release mechanism was Springfast item number C05-021-010, which has an OD of 3.8 mm, an ID of 2.7 mm, and a nominal spring load of 14.2 N. Another compression spring was purchased as an alternative, C04-014-010, but the alternative option was not needed as the C05-021-010 spring successfully operated the release mechanism without issues.

The outer (echogenic) needle used in the prototype was a Havel's Echoblock PTC needle, item number 3-1149-18, with an 18-gauge size and 89 mm shaft length. The inner (piercing) needle was an Air-Tite premium hypodermic, single-use needle, SKU number N224, with a 22-gauge size and a 102 mm shaft length.

A single vented screw (hollow with cylindrical openings on both ends) was purchased from UCComponents, item number C-1016, with a vent diameter of 1.3 mm, and a length of 25 mm.

Screws and nuts from McMaster-Carr secured the casing in the prototype embodiment. We used six narrow "cheesehead" slotted screws (91800A224), and six high hex nuts (90725A025).

Alternative Embodiments

Alternative embodiments can include one or more of the following optional features: A quick unlocking mechanism for easy needle loading. A pre-packaged device with needles already in place. A twisting screw set inside or below the plunger to allow the operator to extend or shorten the plunger, to adjust the distance that the piercing needle travels. A rod attached to the twisting portion of the screw, leading outside the casing, could also adjust the distance that the piercing needle travels; the rod could be movable up to a certain angle in either direction horizontally, but constrained by the housing casing with a visual indicator to correlate the angle with the adjusted distance the piercing needle travels. Other ergonomically-shaped devices can be used, such as devices having a size and shape similar to those of typical highlighter markers or ink pens (or even smaller). The release mechanism could be repositioned to a more ergonomic location. The release mechanism could be a button rather than a lever. A coiled guidewire could be attached, configured to unwind directly through the device instead of requiring the operator to manually feed a guidewire into the device after the needle has pierced the vein.

Miscellaneous

The complete disclosures of all references cited in this specification are hereby incorporated by reference, as is the complete disclosure of the priority application, U.S. provisional application 62/746,791. In the event of an otherwise irreconcilable conflict, however, the present specification shall control.

A note concerning interpretation of the Claims and the specification: To say that a device or a component is "adapted for" a particular use, method, or step (or similar language) signifies that the device or component is capable of and is suitable for carrying out the stated use, method, or step. The language "adapted for" does not, however, imply that the device or component must necessarily be carrying out that use, method, or step at any particular time. The language "adapted for" is intended as a meaningful and significant limitation: It indicates that the device or component is capable of and is suitable for carrying out the use, method, or step; regardless of whether it is actually doing so at any given time. By contrast, a device or component that is not capable of, or that is not suitable for carrying out the use, method, or step would not satisfy the "adapted for" limitation. The language "adapted for" is thus an apparatus limitation, not a method limitation per se.

What is claimed:

1. A device for controllably inserting a piercing needle into the lumen of a vein of a living mammalian patient; wherein said device comprises a casing, a piercing needle, an echogenic needle, a spring, and a release; wherein:
   (a) said piercing needle is adapted to penetrate the wall of a vein, into the lumen of the vein; wherein said piercing needle has a hollow interior through which a guidewire or other flexible line may pass after said piercing needle has penetrated into the lumen of the vein;
   (b) said echogenic needle is reflective to ultrasound, so that the position of said echogenic needle is adapted to be monitored ultrasonically; and said echogenic needle has a hollow interior adapted to be traversed by said piercing needle;
   (c) said spring can assume a compressed state or a relaxed state; wherein said spring is mechanically connected to said piercing needle; and wherein a sudden release of said spring from the compressed state to the relaxed state causes the spring to impart to said piercing needle a force and a velocity sufficient for said piercing needle to penetrate the wall of the vein;
   (d) said release is adapted to release said spring from the compressed state to the relaxed state when said release is engaged by a user;
   (e) said casing holds said piercing needle, said echogenic needle, said spring, and said release; and said casing comprises one or more mechanical restraints that control a distance said piercing needle can traverse in response to force imparted by said spring;
   wherein said device is adapted to be used as follows: the user inserts said echogenic needle in the vicinity of a vein of a mammalian patient; guided by ultrasound imaging, the user directs said echogenic needle to the surface of the vein; when said echogenic needle is on or near the surface of the vein, the user activates said release; once said release is activated, said spring is released from the compressed state to the relaxed state, imparting a force and a velocity to said piercing needle sufficient for said piercing needle to penetrate the wall of the vein; said piercing needle exits the interior of said echogenic needle and penetrates into the vein, stopping at a distance determined by said restraints on said casing, and coming to rest within the lumen of the vein, without piercing a wall of the vein a second time; a guidewire or other flexible line is then introduced into the lumen of the vein through the hollow interior of said piercing needle; the piercing needle is then withdrawn from the vein, leaving the guidewire or other flexible line in place in the lumen of the vein; a catheter is then introduced into the lumen of the vein over the flexible line; and the flexible line is then withdrawn from the vein, leaving the catheter in place in the lumen of the vein.

2. The device of claim 1, wherein said device additionally comprises a guidewire or other flexible line stored within or on said casing; and wherein said guidewire or other flexible line is adapted to be deployed through the hollow interior of said piercing needle into the lumen of the vein when said piercing needle is positioned within the lumen of the vein.

3. The device of claim 1, additionally comprising one or more controls allowing the user to adjust one or more of the following: the force imparted to said piercing needle once said release is activated, the velocity imparted to said piercing needle once said release is activated, and the distance said piercing needle traverses in response to force imparted by said spring once said release is activated.

4. The device of claim 1, wherein all components of said device are dimensionally stable under conditions of temperature, pressure, humidity, and time used for standard medical autoclaving.

5. The device of claim 1, wherein said device has been autoclaved, packaged, and stored in a sterile condition.

6. The device of claim 5, wherein said autoclaved and packaged device is adapted for a single use with a single patient, and then to be discarded following the single use.

7. The device of claim 1, wherein said device is adapted for multiple use with multiple patients; wherein said device is adapted to have said piercing needle and said echogenic needle replaced between uses; and wherein said device is adapted to be autoclaved between uses.

8. The device of claim 1 wherein, when said device is used repeatedly under identical conditions, the performance of said device is repeatable at least 95% of the time within a precision better than ±5% in each of three measures: (a) the distance traveled by said piercing needle once said release is activated, (b) the velocity imparted to said piercing needled once said release is activated, and (c) the force that said piercing needle applies to a vein once said release is activated.

* * * * *